US00PP25887P3

(12) United States Plant Patent

Klemm et al.

(10) Patent No.: US PP25,887 P3

(45) Date of Patent: Sep. 8, 2015

(54) *CALIBRACHOA* PLANT NAMED 'KLECA12236'

(50) Latin Name: ***Calibrachoa* sp.**
Varietal Denomination: KLECA12236

(71) Applicant: Klemm+Sohn GmbH & Co. KG, Stuttgart (DE)

(72) Inventors: Nils Klemm, Stuttgart (DE); Anita Stöver, Ostfildern (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 178 days.

(21) Appl. No.: 13/987,403

(22) Filed: Jul. 22, 2013

(65) Prior Publication Data

US 2015/0026853 P1 Jan. 22, 2015

(51) Int. Cl.
*A01H 5/02* (2006.01)

(52) U.S. Cl.
USPC ..... Plt./413

(58) Field of Classification Search
USPC ..... Plt./413
See application file for complete search history.

(56) References Cited

PUBLICATIONS

Ball Seed MiniFamous Compact Blue 14 *Calibrachoa*, retrieved on Mar. 5, 2014, retrieved from the Internet at <http://www.ballseed.com/Growers/plant_info.aspx?phid=066005976014196> one page.*

Esbenshade's Greenhouses, Inc. 2010 Spring Prefinished Variety List, 5 pp.*

Soos Grower Resources LLC Mast Young Plants Spring Liner Program 2013/2014 Season, pp. 1-8.*

* cited by examiner

*Primary Examiner* — June Hwu

(74) *Attorney, Agent, or Firm* — James M. Weatherly; Barbara Campbell; Cochran Freund & Young LLC

(57) ABSTRACT

A new *Calibrachoa* plant particularly distinguished by having a blue flower color and a compact, mounding form with a semi-trailing plant habit, is disclosed.

1 Drawing Sheet

Genus and species: *Calibrachoa* sp.
Variety denomination: 'KLECA12236'.

BACKGROUND OF THE NEW PLANT

The present invention comprises a new and distinct variety of *Calibrachoa*, botanically known as *Calibrachoa* sp, and hereinafter referred to by the variety name 'KLECA12236'. 'KLECA12236' originated from a controlled-cross between the proprietary female *Calibrachoa* variety 'CA-2004-X030' (unpatented) and the male *Calibrachoa* variety 'KLECA08170' (U.S. Plant Pat. No. 21,061).

In May 2008, two *Calibrachoa* parental lines, 'CA-2004-X030' and the male *Calibrachoa* variety 'KLECA08170' were crossed via a controlled-cross in Stuttgart, Germany and seeds were obtained. The seeds were sown and plants were grown for evaluation. A plant line was selected in May 2009 and subsequently named 'KLECA12236'. In May 2009, 'KLECA12236' was first vegetatively propagated by tip cuttings and in vitro shoot tips in Stuttgart, Germany. 'KLECA12236' was found to reproduce true to type in successive generations of asexual propagation via tip cuttings.

CROSS REFERENCE TO RELATED APPLICATIONS

Plant Breeder's Rights for 'KLECA12236' were applied for in Canada on Jan. 23, 2013, Application No. 13-7851 and in Switzerland on Jun. 6, 2013 as Application No. 13-2872.

'KLECA12236' has not been made publicly available or sold more than one year prior to the filing date of this application.

SUMMARY

The following are the most outstanding and distinguishing characteristics of this new variety when grown under normal horticultural practices in Stuttgart, Germany.

1. Blue flower color; and
2. A compact, mounding form with a semi-trailing plant habit.

DESCRIPTION OF THE PHOTOGRAPH

This new *Calibrachoa* plant is illustrated by the accompanying photograph which shows a close-up of the flowers. The photograph is of a five-month-old plant grown in Stuttgart, Germany in May 2012. The colors shown are as true as can be reasonably obtained by conventional photographic procedures.

DESCRIPTION OF THE NEW VARIETY

The following detailed descriptions set forth the distinctive characteristics of 'KLECA12236'. The data which define these characteristics were collected from asexual reproductions carried out in Stuttgart, Germany. Data was collected on five-month-old plants grown in Stuttgart, Germany in May 2013. Color references are to The R.H.S. Colour Chart of The Royal Horticultural Society of London (R.H.S.), 5$^{th}$ edition (2007).

Classification:
*Family*.—Solanaceae.
*Species*.—*Calibrachoa* sp.
*Common name*.—*Calibrachoa*.
Parentage:
*Female*.—Proprietary *Calibrachoa* line 'CA-2004-X030'.
*Male*.—*Calibrachoa* line 'KLECA08170' (U.S. Plant Pat. No. 21,061).
Plant description:
*Life cycle*.—Annual.
*Form*.—Compact, mounding.
*Habit*.—Semi-trailing.
*Height* (*from soil line to top of foliage*).—6.0 cm.
*Spread*.—29.0 cm.
Propagation: Vegetatively propagated.
*Type cuttings*.—Tip cuttings.
*Time to produce a rooted cutting*.—3 weeks.
Stems:
*Stem diameter*.—2.0 mm.
*Stem length*.—13.0 cm. From soil line to first node: 1.5 cm. Total length: 15.0 cm.
*Internode length*.—2.0 cm.
*Stem color*.—RHS 144C.
*Pubescence*.—Absent.
Leaves:
*Arrangement*.—Alternate, simple, sessile.
*Shape*.—Elliptic.
*Apex*.—Obtuse to slightly acute.
*Base*.—Attentuate.
*Margin*.—Entire.
*Surface*.—Smooth.
*Surface pubescence*.—Absent.
*Venation*.—Pinnate.
*Venation color*.—Upper surface: RHS 145B. Lower surface: RHS 145A.
*Length*.—2.5 cm.
*Width*.—0.7 cm.
*Color*.—Upper surface: RHS 146B. Lower surface: RHS 146D.
*Fragrance*.—Absent.
Flowers: Single flowers.
*Flowering habit*.—Flowers face upright, single, axillary.
*Flower type*.—Determinate inflorescence.
*Flowering requirements*.—A minimum of light sun is required.
*Flowering season*.—Entire summer till first frost.
*Duration of flowers*.—6 days.
*Corolla*.—Smooth texture.
*Shape*.—Funnel-shaped.
*Fragrance*.—Absent.
Flower buds:
*Surface*.—Smooth.
*Length*.—2.0 cm.
*Diameter*.—0.6 cm.
*Shape*.—Irregular to oblong.
*Color*.—RHS N82A.
Peduncle:
*Length*.—1.5 cm.
*Diameter*.—0.1 cm.
*Color*.—RHS 145A.
*Texture*.—Rough.
*Anthocyanin color*.—RHS N79C.
Flower description:
*Flower depth*.—2.0 cm.
*Flower tube length*.—1.5 cm.
*Flower tube diameter*.—0.9 cm.
*Flower diameter*.—4.0 cm.
*Pedicel color*.—RHS 145A.
*Calyx*.—Funnel-shaped.
Sepals:
*Shape*.—Lanceolate.
*Apex*.—Broad acute.
*Margin*.—Entire.
*Length*.—2.3 cm.
*Diameter*.—0.4 cm.
*Sepal color*.—Upper surface: RHS 144A. Lower surface: RHS 144A.
Petals:
*Shape*.—Heart-shaped.
*Length*.—2.2 cm.
*Apex*.—Obverse.
*Margin*.—Entire.
*Base*.—Open and fused into the tube.
*Pubescence*.—Absent.
*Lobe length*.—2.1 cm.
*Lobe width*.—1.9 cm.
*Color*.—Lobe color: Upper surface: RHS N87A; venation color RHS 86A. Lower surface: RHS N87C. Corolla tube color: Inner: RHS 5A; venation color RHS 64A. Outer: RHS 5C and RHS 83B.
*Fragrance*.—Absent.
Reproductive organs:
*Stamen number*.—5.
*Stamen color*.—Anther color: RHS 6D. Filament color: RHS 1C. Pollen color: RHS 6C.
*Ovary*.—Placenta arrangement: Ovate. Pistil number: 1. Pistil length: 0.1 cm. Stigma color: RHS 154A. Style length: 0.7 cm. Style color: RHS 149B.
Fruit/seed set: Little seed production.
Disease/insect resistance: None observed.

COMPARISON WITH PARENTAL LINES AND KNOWN VARIETY

'KLECA12236' is distinguished from its parental lines as described in Table 1:

TABLE 1

Comparison with Parental Lines

| Trait | Variety 'KLECA12236' | Female parent 'CA 2004 X 030' | Male Parent 'KLECA08170' |
|---|---|---|---|
| Flower color | RHS N87A | RHS 83A | RHS 85C |

'KLECA12236' is most similar to the *Calibrachoa* plant named 'KLECA08170' (U.S. Plant Pat. No. 21,061). Differences between the two varieties are described in Table 2:

TABLE 2

Comparison with Similar Variety

| Trait | Variety 'KLECA12236' | Commercial line 'KLECA08170' |
|---|---|---|
| Growing habit | Compact and mounding with semi-trailing | Flat trailing |
| Flower color | RHS N87A | RHS 85C |

We claim:

1. A new and distinct variety of *Calibrachoa* plant named 'KLECA12236' as illustrated and described herein.

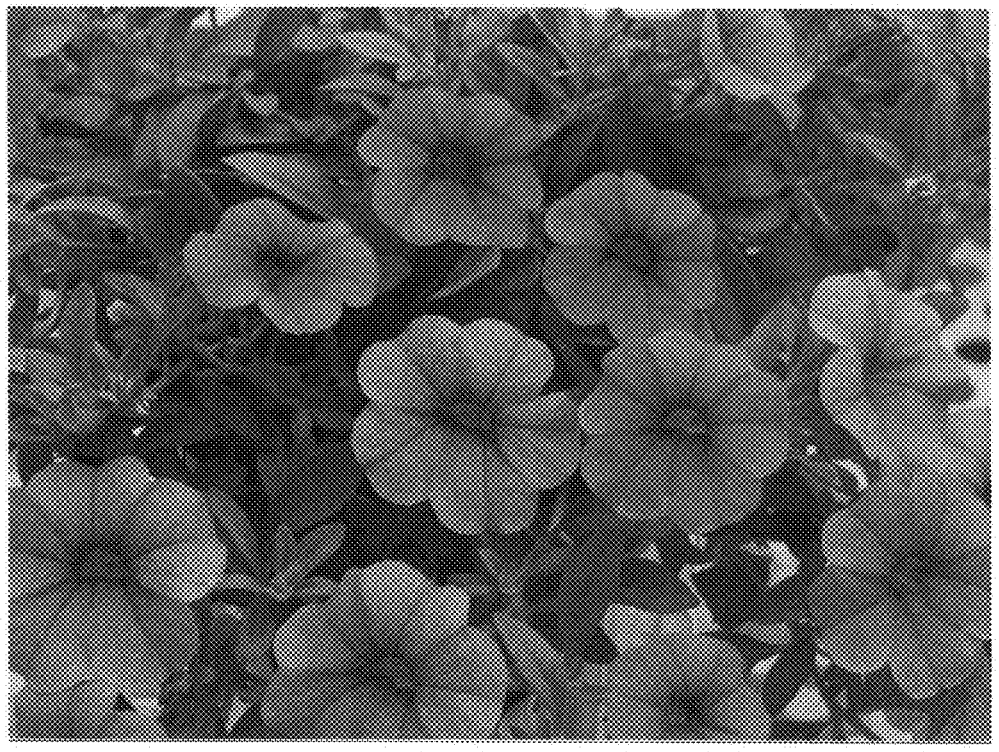

* * * * *